US008795155B2

(12) United States Patent
Kanazawa

(10) Patent No.: US 8,795,155 B2
(45) Date of Patent: Aug. 5, 2014

(54) ELECTRONIC BENDING ENDOSCOPE DEVICE AND ENDOSCOPE SUPPORTING DEVICE

(75) Inventor: Noriaki Kanazawa, Musashino (JP)

(73) Assignee: Olympus Corporation, Tokyo (JP)

( * ) Notice: Subject to any disclaimer, the term of this patent is extended or adjusted under 35 U.S.C. 154(b) by 1456 days.

(21) Appl. No.: 11/886,442

(22) PCT Filed: Mar. 7, 2006

(86) PCT No.: PCT/JP2006/304387
§ 371 (c)(1),
(2), (4) Date: Sep. 14, 2007

(87) PCT Pub. No.: WO2006/098190
PCT Pub. Date: Sep. 21, 2006

(65) Prior Publication Data
US 2008/0154089 A1    Jun. 26, 2008

(30) Foreign Application Priority Data
Mar. 14, 2005    (JP) .................................. 2005-071713

(51) Int. Cl.
*A61B 1/04* (2006.01)
(52) U.S. Cl.
USPC ......................................... 600/102; 248/121
(58) Field of Classification Search
USPC ....................................................... 600/102
See application file for complete search history.

(56) References Cited

U.S. PATENT DOCUMENTS

| | | | | |
|---|---|---|---|---|
| 4,854,301 A | * | 8/1989 | Nakajima | ...................... 600/102 |
| 4,863,133 A | * | 9/1989 | Bonnell | ................... 248/280.11 |
| 5,228,427 A | * | 7/1993 | Gardner, Jr. | ..................... 124/71 |
| 5,441,042 A | * | 8/1995 | Putman | .......................... 600/102 |
| 5,571,072 A | * | 11/1996 | Kronner | ........................ 600/102 |
| 5,766,126 A | * | 6/1998 | Anderson | ...................... 600/102 |

(Continued)

FOREIGN PATENT DOCUMENTS

| | | |
|---|---|---|
| JP | 63-122416 | 5/1988 |
| JP | 2003-010099 | 1/2003 |

(Continued)

*Primary Examiner* — Matthew J Kasztejna
(74) *Attorney, Agent, or Firm* — Scully, Scott, Murphy & Presser, P.C.

(57) ABSTRACT

The present invention provides an electric bending endoscope device which has an endoscope supporting device. The endoscope supporting device is provided with an electric bending unit and an insertion portion detachably configured in a state that an electric bending endoscope is always supported to improve an efficiency of an operation to be performed before and after an inspection and to reduce the work or burdens of the users, and in the state that the endoscope is being supported, the endoscope can be used, and similarly, the supporting device can be stored in the state that the endoscope is being supported. For the purpose, the electric bending endoscope device includes an endoscope 11 having an observation function and a treatment function of the inside of a body cavity, and an endoscope supporting device 40 having a first moving member (hinge 46) capable of moving up and down the endoscope in a direction perpendicular to a floor, a second moving member (arm movable portion 43 and slide guide 44) capable of moving the endoscope in a horizontal direction with respect to the floor, a first supporting portion (bearing portion 42*a*) for permitting the endoscope to rotate around an axis and supporting the endoscope, and a second supporting portion (supporting portion 42) for supporting the endoscope movably in vertical and horizontal directions.

2 Claims, 7 Drawing Sheets

(56) References Cited

U.S. PATENT DOCUMENTS

| | | | |
|---|---|---|---|
| 5,888,190 A * | 3/1999 | Meyer et al. | 600/102 |
| 6,569,084 B1 | 5/2003 | Mizuno et al. | |
| 6,802,809 B2 | 10/2004 | Okada | |
| 7,556,626 B2 * | 7/2009 | Ueda et al. | 606/1 |
| 2002/0103418 A1 | 8/2002 | Maeda et al. | |
| 2004/0097966 A1 | 5/2004 | Nakamura | |
| 2004/0172012 A1 | 9/2004 | Otsuka et al. | |
| 2005/0165271 A1 * | 7/2005 | Shioda et al. | 600/102 |
| 2006/0235268 A1 * | 10/2006 | Elsie et al. | 600/102 |

FOREIGN PATENT DOCUMENTS

| | | |
|---|---|---|
| JP | 2003-061968 | 3/2003 |
| JP | 2004-275203 | 10/2004 |
| JP | 2005-007189 | 1/2005 |

\* cited by examiner

ELECTRONIC BENDING ENDOSCOPE DEVICE AND ENDOSCOPE SUPPORTING DEVICE

TECHNICAL FIELD

The present invention relates to an electric bending endoscope device, and more particularly, the invention relates to an endoscope supporting device which has functions to support and house an electric bending endoscope which electrically drives a bending portion provided in an insertion portion of the endoscope to bend, and relates to an electric bending endoscope device which includes the endoscope supporting device.

BACKGROUND ART

Conventionally, endoscopes are widely used, for example, to observe an organ in a body cavity by inserting an elongated insertion portion into the body cavity, or to perform various curative treatments using a treatment instrument which is inserted into a treatment instrument insertion channel if necessary.

Generally, such conventional endoscopes are provided with a bending portion which can be bent in vertical and horizontal directions at a distal end side of an insertion portion. A bending wire extending from an operation portion side is connected to a predetermined potion of the bending portion. The bending portion can be bent in a desired direction when a pulling operation or a loosening operation of the bending wire is performed using an operation member of an operation portion side.

Generally, in the operation of the bending wire in the conventional endoscope, the operation member which is provided in the operation portion is manually operated to mechanically operate the bending wire. However, in recent years, various electric bending endoscope devices have been proposed in which the pulling operation of the bending wire is performed using electric bending drive means such as an electric motor.

In an endoscope in such an electric bending endoscope device, the electric bending drive means such as an electric motor is disposed in the operation portion or the like. Accordingly, the operation portion tends to be largely increased in size and also increased in weight. Then, when users perform the bending operation using the operation member provided to the operation portion while supporting the operation portion with one hand, the users are tend to be burdened. This causes difficulties in performing the operation.

Accordingly, in view of the above, in the electric bending endoscope device, endoscope supporting devices for supporting an operation portion of an endoscope system in use have been proposed to reduce the burdens to the users when using the device, for example, in Japanese Unexamined Patent Application Publication No. 63-122416.

The endoscope supporting device disclosed in Japanese Unexamined Patent Application Publication No. 63-122416 includes a supporting portion which supports an operation portion of an endoscope or the periphery of the operation portion and a displacement mechanism which is formed by a flexible polyarticular arm to enable the operation portion to rotate and displace or to enable translational displacement of the operation portion.

However, the endoscope supporting device disclosed in the above Japanese Unexamined Patent Application Publication No. 63-122416 is configured to support the endoscope being used at a predetermined position during the use of the endoscope. Thus, the endoscope supporting device is not appropriate for the use of, for example, housing the endoscope in the supported state or supporting the endoscope in a state just before the start of the use, that is, a so-called usage standby state.

For example, after an endoscopy is finished, the endoscope has to be detached from the supporting device to be washed. In the method disclosed in the above publication, the work of detaching the endoscope is troublesome. Further, before an endoscopy is performed, the washed endoscope has to be attached to the supporting device, and this operation is also troublesome.

Moreover, if the endoscope is electrically operated, the endoscope tends to be larger and heavier. Then, burdens in attaching the endoscope to the supporting device before the endoscopy and in detaching the endoscope after the endoscopy are further increased. In addition to the above, if a universal code extending from the endoscope is disposed along the arm of the supporting device, an attaching operation of the endoscope to the supporting device and a detaching operation of the endoscope to the supporting device have to be performed.

Meanwhile, conventionally, instruments such as a hanger used to store treatment instruments, not only the endoscope but also other instruments, or support the instruments in a standby state have been practically used. However, such conventional instruments like the hanger are not used when the endoscope or the treatment instruments are being used, but the instruments are configured to store the endoscope or the instruments or to be used in the standby state.

Further, when the instruments such as the hanger are used to store the endoscope, if the supporting device is used, during the use of the endoscope, it is necessary to provide a space to place the instruments such as the hanger which store the instruments.

The present invention has been made in view of the above, and an object of the invention is to provide an endoscope supporting device and an electric bending endoscope device which has the endoscope supporting device, the endoscope supporting device is provided with an electric bending unit and an insertion portion detachably configured in a state that an electric bending endoscope is always supported to increase an efficiency of an operation to be performed before an inspection and to reduce the work or burdens of the users, and in the state that the endoscope is being supported, the endoscope can be used, and similarly, the supporting device can be stored in the state that the endoscope is being supported.

DISCLOSURE OF INVENTION

Means for Solving the Problem

To achieve the above objects, an electric bending endoscope device according to a first aspect of the present invention includes an endoscope having an observation function and a treatment function of the inside of a body cavity, and an endoscope supporting device having a first moving member capable of moving up and down the endoscope in a direction perpendicular to a floor, a second moving member capable of moving the endoscope in a horizontal direction with respect to the floor, a first supporting portion for permitting the endoscope to rotate around an axis and supporting the endoscope, and a second supporting portion for supporting the endoscope movably in vertical and horizontal directions.

An electric bending endoscope device according to a second aspect of the present invention includes a first moving member capable of moving up and down an endoscope in a direction perpendicular to a floor, a second moving member capable of moving the endoscope in a horizontal direction with respect to the floor, a first supporting portion which permits the endoscope to rotate around an axis and supports the endoscope, and a second supporting portion which supports the endoscope movably in vertical and horizontal directions.

BEST MODE FOR CARRYING OUT THE INVENTION

Hereinafter, the invention will be described with reference to illustrated embodiments.

Figure 1:
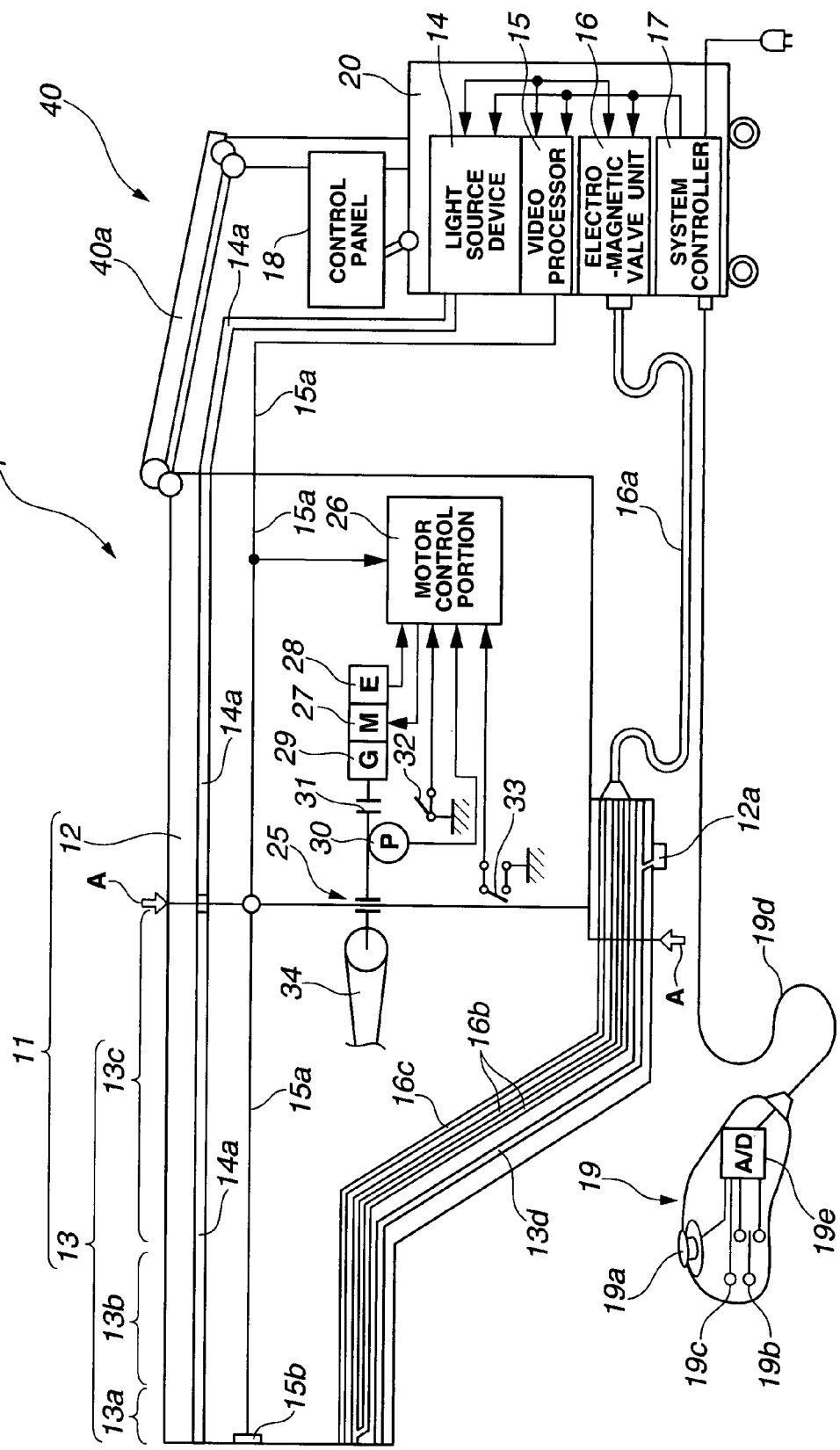
FIG. 1 is a structural view schematically illustrating a whole structure of an electric bending endoscope device according to an embodiment of the present invention.
Figure 2:
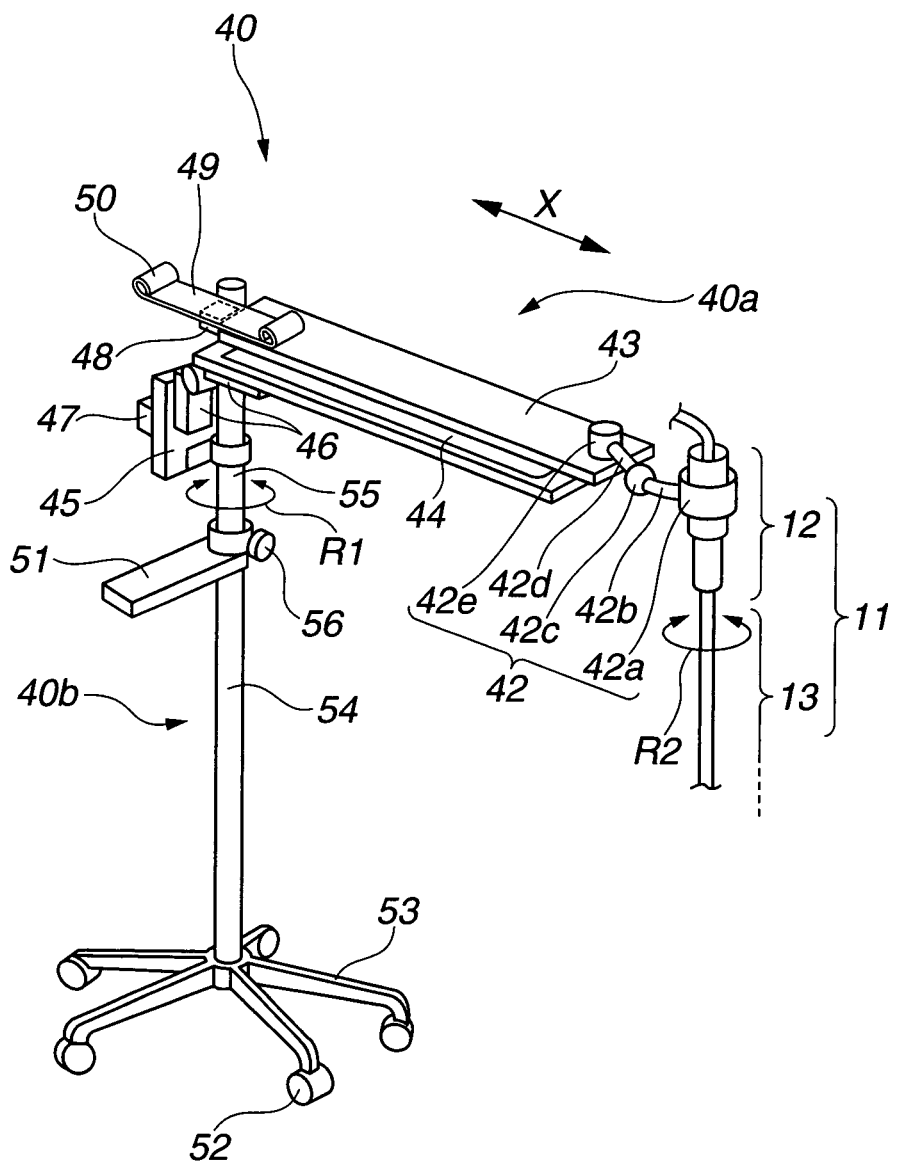
FIG. 2 is an outside view illustrating a state in which an endoscope supporting device in the electric bending endoscope device of FIG. 1 is in a usage state.
Figure 3:
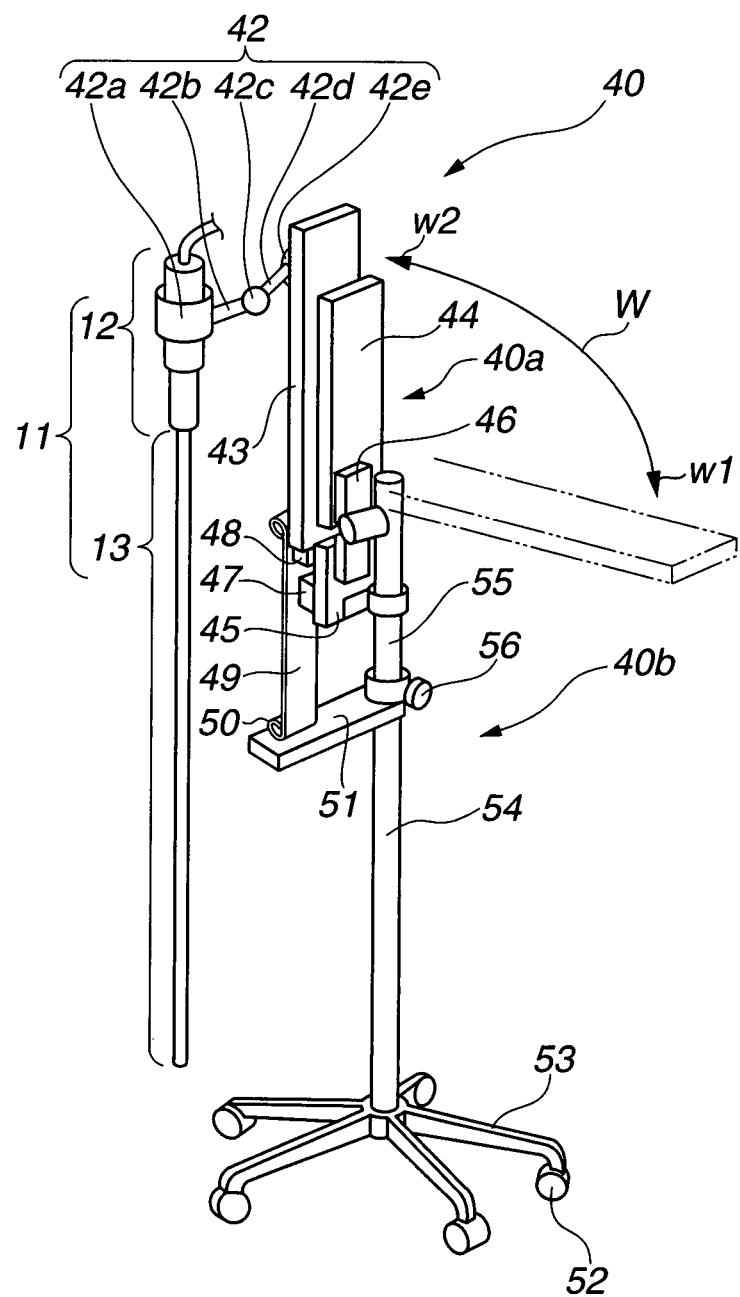
FIG. 3 is an outside view illustrating a state in which the endoscope supporting device in the electric bending endoscope device of FIG. 1 is in a usage standby state.
Figure 4:
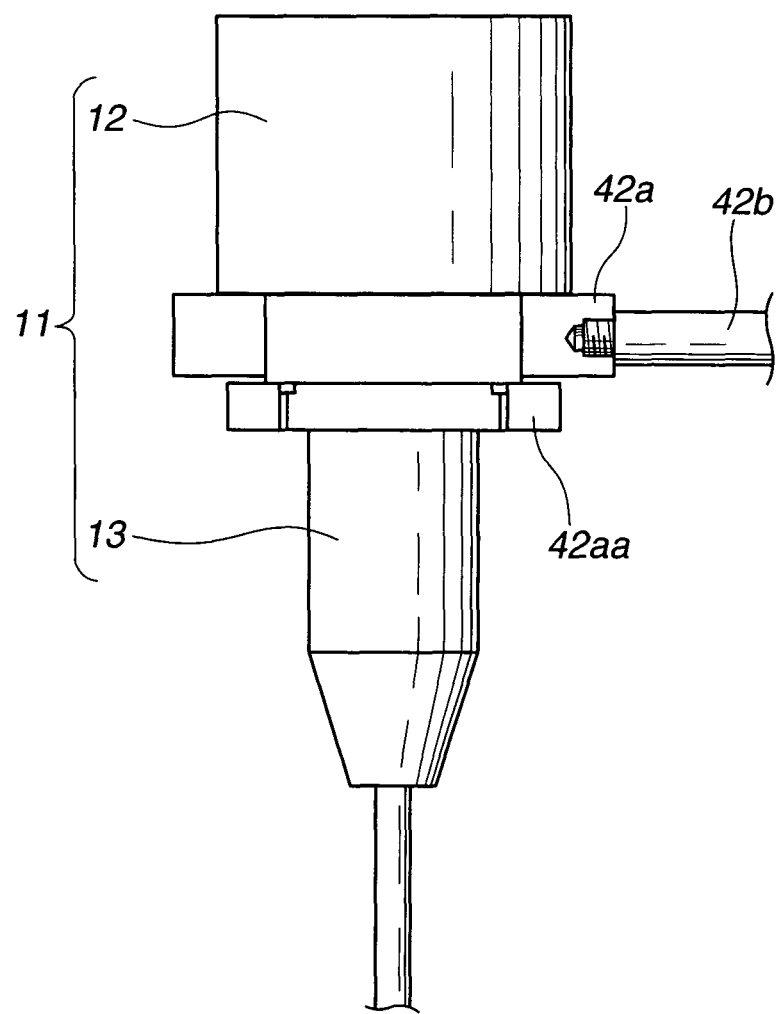
FIG. 4 is an enlarged side view of a substantial part illustrating an enlarged neighborhood of a bearing portion of a storing portion in the endoscope supporting device of FIGS. 2 and 3.
Figure 5:
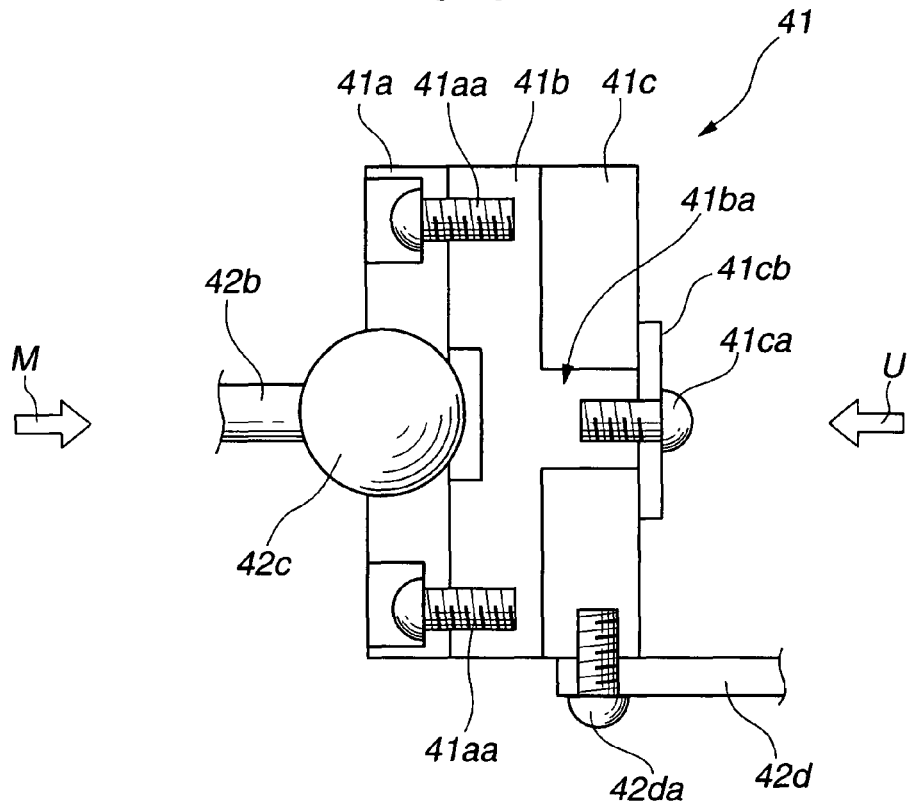
FIG. 5 is an enlarged cross sectional view of a substantial part illustrating an enlarged neighborhood of a ball joint of the storing portion in the endoscope supporting device of FIGS. 2 and 3, and illustrating a longitudinal section viewed from a side surface.
Figure 6:
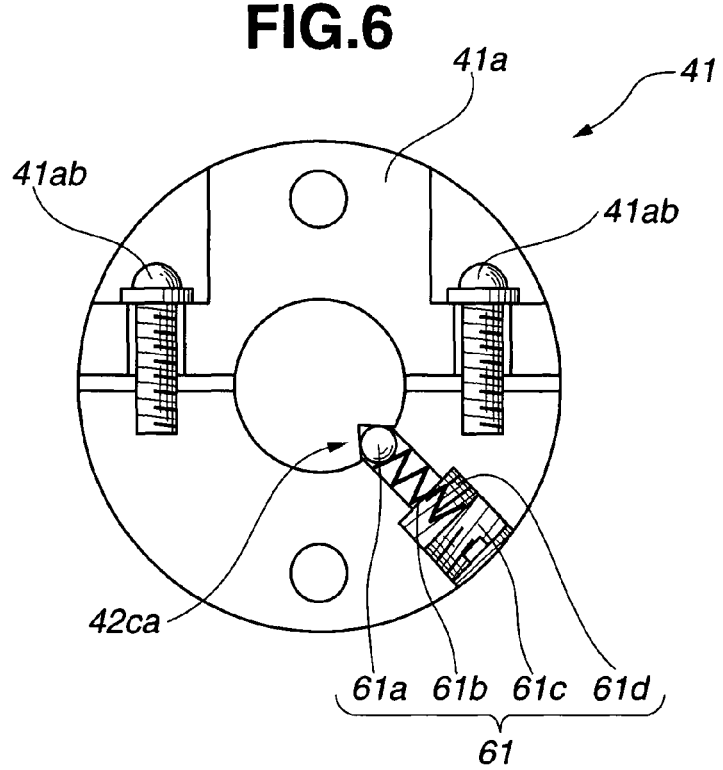
FIG. 6 is an enlarged cross sectional view of a substantial part illustrating an enlarged neighborhood of the ball joint of the storing portion in the endoscope supporting device of FIGS. 2 and 3, and illustrating a longitudinal section viewed from a front side (side of the arrow M of FIG. 5).
Figure 7:
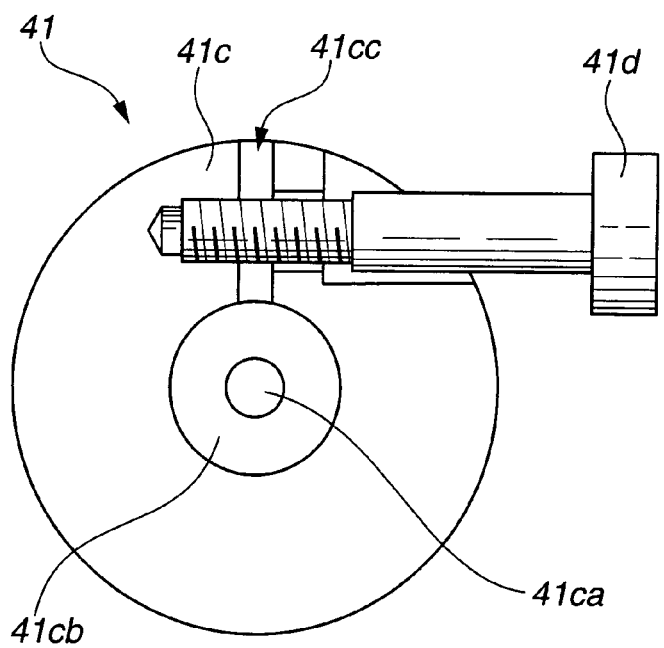
FIG. 7 is an enlarged cross sectional view of a substantial part illustrating an enlarged neighborhood of the ball joint of the storing portion in the endoscope supporting device of FIGS. 2 and 3, and illustrating a longitudinal section viewed from a back side (side of the arrow U of FIG. 5).
Figure 8:
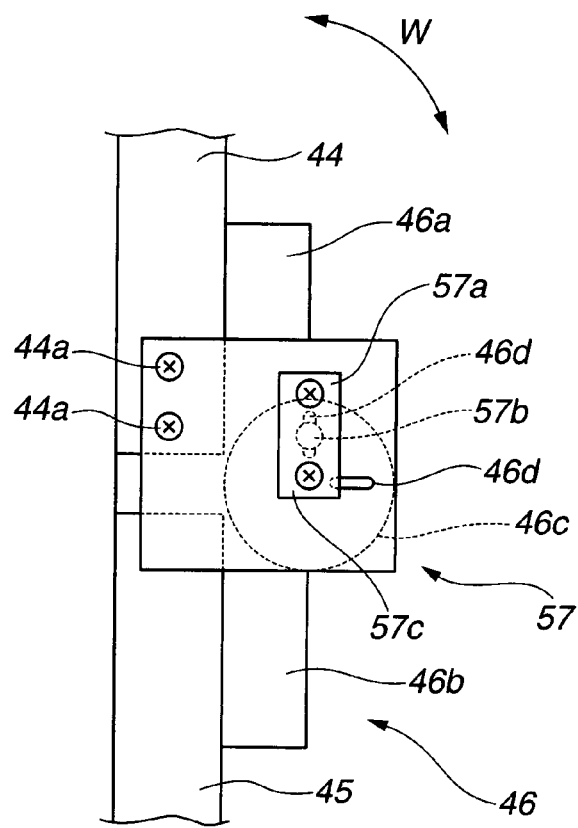
FIG. 8 is an enlarged side view illustrating an enlarged neighborhood of an attaching portion of a hinge of an arm portion in the endoscope supporting device of FIGS. 2 and 3.
Figure 9:
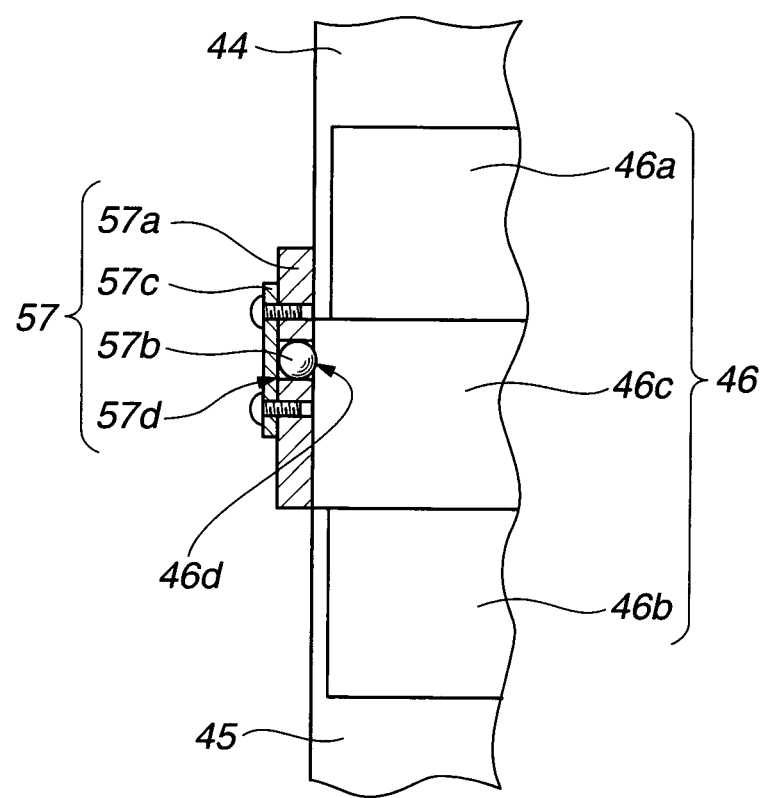
FIG. 9 is an enlarged elevational view illustrating an enlarged neighborhood of the attaching portion of the hinge of the arm portion in the endoscope supporting device of FIGS. 2 and 3, and illustrating a sectional view of a hinge angle adjustment mechanism.

FIG. 1 is a structural view schematically illustrating a whole structure of an electric bending endoscope device according to an embodiment of the present invention. FIGS. 2 and 3 are outside views illustrating a whole structure of an endoscope supporting device in the electric bending endoscope device according to the present embodiment of the invention. FIG. 2 illustrates a state that the endoscope supporting device is in the usage state. FIG. 3 illustrates a state that the endoscope supporting device is not used (usage standby state). FIGS. 4 to 9 are enlarged views of substantial parts illustrating enlarged parts of the endoscope supporting device of FIGS. 2 and 3. FIG. 4 is a side view illustrating a neighborhood of a bearing portion of a storing portion which is provided at a distal end of the endoscope supporting device of FIGS. 2 and 3 to support the electric bending endoscope device. FIGS. 5 to 7 are enlarged cross sectional views of substantial parts illustrating enlarged neighborhoods of a ball joint of the storing portion in the endoscope supporting device of FIGS. 2 and 3. FIG. 5 illustrates a longitudinal section viewed from a side surface, FIG. 6 illustrates a longitudinal section viewed from a front side (the side of the arrow M of FIG. 5), FIG. 7 illustrates a longitudinal section viewed from a back side (the side of the arrow U of FIG. 5) respectively. FIGS. 8 and 9 are views illustrating enlarged neighborhoods of an attaching portion of a hinge of an arm portion in the endoscope supporting device of FIGS. 2 and 3. FIG. 8 is a view illustrating the neighborhood of the hinge viewed from a side surface. FIG. 9 is a view illustrating the neighborhood of the hinge viewed from a front surface, in which a cross section of a hinge angle adjustment mechanism and the internal structure are illustrated.

An electric bending endoscope device 1 according to the present embodiment includes as shown in FIG. 1, an electric bending endoscope 11 which has an observation function and a treatment function of the inside of a body cavity, and which has an elongated insertion portion 13 to be inserted into the body cavity, a bending drive unit 12 which is detachably connected to a proximal end side of the insertion portion 13, which functions as electric bending means, and which has a bending drive member in the unit, and an operation unit 19 which is provided as an unit separately from the bending drive unit 12 and electrically connected to the bending drive unit 12, and the like. Further, the electric bending endoscope device 1 includes a light source device 14 which provides illumination light flux to be emitted toward the front surface of the distal end portion of the insertion portion 13, a video processor 15 which receives a video signal from an image pickup unit 15b which is provided at the distal end of the insertion portion 13 and performs a predetermined signal process, and an electromagnetic valve unit 16 which performs a control of an air supply/water supply operation or a suction operation through an air supply/water supply channel 16b or a suction channel 16c or the like which are provided in the insertion portion 13. Further, the electric bending endoscope device 1 includes a system controller 17 which performs a drive control of the bending drive unit 12 and totally controls the light source device 14, the video processor 15, the electromagnetic valve 16, and the like, a control panel 18 which has a display portion which receives the video signal from the video processor 15 and displays a predetermined endoscopic image and which can input various operation instructions using an operation portion provided on a display screen of the display portion, an endoscope supporting device 40 (see FIGS. 2 to 9 for detailed information) which has an arm portion 40a which movably supports the electric bending endoscope device 11 and the like, a cart 20 which houses the light source device 14, the video processor 15, the electromagnetic valve 16, the system controller 17, the control panel 18, and the like and has casters, for example, in order to freely move on a floor while mounting the devices.

The insertion portion 13 and the bending drive unit 12 are detachable at a detaching portion shown by a reference numeral A in FIG. 1 through an engaging member 25 which functions as engaging means. As the engaging member 25 which functions as the engaging means, for example, a dog clutch is used. With the engaging member 25 which functions as the engaging means, the insertion portion 13 and the bending drive unit 12 are detachably and consecutively connected with each other and when the insertion portion 13 and the bending drive unit 12 are consecutively connected with each other, a driving force from the bending drive unit 12 is transmitted to a side of the insertion portion 13.

The insertion portion 13 includes a distal end rigid portion 13a which has an image pickup unit 15b which has an image pickup optical system (not shown), an image pickup device such as a CCD, or the like in the unit and which is formed at a most distal end side, a bending portion 13b which is consecutively connected to a proximal end side of the distal end rigid portion 13a and which can perform a bending operation in vertical and horizontal directions under the drive control of the bending drive unit 12 which is controlled according to a bending operation instruction issued by the operation portion 19, and a flexible tube portion 13c which is consecutively connected to a proximal end side of the bending portion 13b and which is formed in an elongated shape.

Into the insertion portion 13, an angle wire 34 which is driven in response to a driving force supplied from the bending drive unit 12 is inserted. The angle wire 34 is connected to a distal end side of the bending portion 13b (with respect to a connection portion, not particularly shown in the drawings). Thus, if the angle wire 34 is driven in response to the driving force supplied from the bending drive unit 12, the bending portion 13b can be bent in vertical and horizontal directions.

Further, into the insertion portion 13, as described above, the air supply/water supply channel 16b and the suction channel 16c are inserted. At fore sides of distal end sides of the air supply/water supply channel 16b and the suction channel 16c, an air supply/water supply opening and a suction opening are opened (not particularly shown).

Further, through the insertion portion 13, a forceps channel 13d through which treatment instruments such as a forceps are inserted is inserted. At a fore side of a distal end side of the forceps channel 13d, a forceps opening is opened (not particularly shown). A proximal end side of the forceps channel 13d is connected to a forceps insertion opening 12a which is formed in the vicinity of the detaching portion A of the bending drive unit 12. Thus, the treatment instruments such as the forceps which are inserted from the forceps insertion opening 12a can be inserted through the forceps channel 13d and can be protruded from the fore side of the distal end side of the insertion portion 13.

The bending drive unit 12 functions as the bending drive means and the bending drive member which includes an electric motor 27 and various members configured to transmit or detach a power generated by the electric motor 27.

The bending drive unit 12 includes the electric motor 27 which generates driving force, a motor control portion 26 which performs a total control of the bending drive unit 12 which includes the electric motor 27, an encoder 28 which converts an operation status such as a rotational speed or a rotational amount of the electric motor 27 as data, a deceleration gear 29 which decelerates a rotational power of the electric motor 27, an electromagnetic clutch 31 which is connected to the deceleration gear 29 and transmits the rotational power of the electric motor 27 to a side (functions as engaging means and engaging member 25) of the insertion portion 13, a potentiometer 30 which functions as rotational position detection means and a rotational position detection member, a clutch state detection switch 32 which detects a state of the electromagnetic clutch 31, a detaching state detection switch 33 which detects an engaging state of the insertion portion 13 and the bending drive unit 12, and the like.

To the light source device 14, a light guide 14a is connected. The light guide 14a is disposed such that the light guide 14a is inserted through the inside of the bending drive unit 12 and the insertion portion 13 and extends to the distal end portion of the insertion portion 13. In such a case, the light guide 14a can be detached at the detaching portion A of the bending drive unit 12 and the insertion portion 13 and disposed to communicate with each other when the bending drive unit 12 and the insertion portion 13 are engaged with each other. Thus, the illumination light flux supplied from the light source device 14 is illuminated through the light guide 14a from the distal end portion of the insertion portion 13 toward the front.

To the video processor 15, a signal cable 15a for transmitting a video signal from the image pickup unit 15b is connected. The signal cable 15a extends from the image pickup unit 15b at the distal end of the insertion portion 13, is inserted in the inside of the insertion portion 13 and the bending drive unit 12, and is connected to a predetermined terminal of the video processor 15. In such a case, the signal cable 15a can be detached at the detaching portions A of the bending drive unit 12 and the insertion portion 13, and in a state that the bending drive unit 12 and the insertion portion 13 are engaged with each other, the cable 15a and the processor 15 are electrically connected. Thus, connection connectors or the like (not particularly shown) are provided at respective detaching portions A of the bending drive unit 12 and the insertion portion 13.

To the video processor 15, a control panel 18 is electrically connected. Thus, a video signal outputted from the video processor 15 is transmitted to the control panel 18. In response to the signal, the control panel 18 displays a predetermined endoscopic image using a display portion.

To the electromagnetic valve unit 16, a tube 16a which is consecutively provided to the air supply/water supply channel 16b and the suction channel 16c of the insertion portion 13 is connected. Thus, the electromagnetic valve 16 can communicate with the distal end of the insertion portion 13 through the air supply/water supply channel 16b, the suction channel 16c, and the tube 16a, and if the electromagnetic valve 16 is driven and an air supply/water supply operation or a suction operation is performed, the air supply/water supply or the suction can be performed from the distal end of the insertion portion 13.

The operation portion 19 includes various operation members for generating a bending operation instruction, an air supply/water supply, or a suction operation instruction signal as a separate unit from the bending drive unit 12.

More specifically, the operation portion 19 includes various operation members such as an operation stick 19a for performing a bending operation instruction, an operation button 19b for performing an air supply/water supply instruction, and an operation button 19c for performing a suction operation instruction, an AD converter 19e which is electrically connected to the respective operation members (19a, 19b, 19c), and the like. The AD converter 19e performs an AD conversion, that is, the AD converter 19e receives electric signals generated in the respective operation members (19a, 19b, 19c) and converts into predetermined operation instruction signals.

The operation portion 19 is electrically connected to the system controller 17 through an electric cable 19d. Accordingly, the operation instruction signals generated by the AD converter 19e are transmitted through the electric cable 19d to the system controller 17.

Between the system controller 17 and the light source device 14, the video processor 15, the electromagnetic valve unit 16, and the control panel 18, electrical connections are established respectively. To the system controller 17, the electric cable 19d which extends from the operation portion 19 is also connected. Thus, the respective instruction signals generated by the operations of the respective operation members of the operation portion 19 are transmitted through the electric cable 19d to the system controller 17. In response to the signals, the system controller 17 appropriately transmits control signals for performing controls corresponding to the instruction signals to the respective devices.

In response to the respective operation instruction signals from an operation portion of the control panel 18, the system controller 17 also appropriately transmits control signals for performing controls corresponding to the instruction signals to the respective devices.

As shown in FIGS. 2 and 3, the endoscope supporting device 40 supports the electric bending endoscope 11. That is, the endoscope supporting device 40 can readily displace states with one operation, that is, the endoscope supporting device 40 displaces a usage state (a first state) shown in FIG. 2 that the electric bending endoscope 11 is used while the electric bending endoscope 11 is supported into a usage standby state (a second state) shown in FIG. 3 that the electric bending endoscope 11 is in a standby state before the electric bending endoscope 11 is used while the electric bending endoscope 11 is supported.

In other words, the endoscope supporting device 40 can freely switch between the usage state in that while the electric bending endoscope 11 is supported, the electric bending endoscope 11 can be freely moved in either vertical or horizontal direction, and the usage standby state in which a state is maintained such that while the electric bending endoscope 11 is supported, the movement of the electric bending endoscope 11 is regulated and a vicinity of a distal end portion of the insertion portion 13 of the electric bending endoscope 11 does not come in contact with a floor. Thus, the endoscope supporting device 40 is configured as described below.

That is, the endoscope supporting device 40 includes a supporting portion 40b which has a caster 52 to freely move on the floor, and an arm portion 40a which is fixed to the supporting portion 40b to support the electric bending endoscope 11.

The arm portion 40a in the endoscope supporting device 40 includes a supporting portion 42 which supports the bending drive unit 12 of the electric bending endoscope 11, an arm movable portion 43 which supports the supporting portion 42 in the vicinity of the distal end, which is provided to be movable in a predetermined direction (X direction in FIG. 2) in a predetermined state (usage state), and which is composed of a plate-shaped member or the like, a slide guide 44 which supports the arm movable portion 43 slidably in a direction along the arrow X of FIG. 2, and which is composed of a plate-shaped member, and an arm fixing member 45 which is provided rotatably in a direction along the arrow R1 of FIG. 2 with respect to a predetermined portion (second support rod 55 which will be described below) of the supporting portion 40b. The arm portion 40a also includes hinges 46 which are fixed on one end portion of the respective arm fixing member 45 and the slide guide 44, and which enables the arm portion 40a to move (movement in the direction of the arrow W of FIG. 3) in a vertical direction with respect to the floor, a fixing side magnet (first magnet) 47 which is fixed on a surface of the arm fixing member 45, and an arm side magnet (second magnet) 48 which is fixed on a proximal end surface of the arm movable portion 43, a thin plate shaped constant force spring 49 whose one end is fixed on the proximal end surface of the arm movable portion 43, a third magnet 50 which is provided at a distal end side of the constant force spring 49, a fourth magnet 51 which is fixed on a predetermined portion of the second support rod 55 (description will be made below) in the supporting portion 40b, and which attracts the third magnet 50 at a predetermined state (usage standby state), and the like.

The supporting portion 42 functions as supporting means that is, the supporting portion 42 supports the electric bending endoscope 11, which is supported at the distal end, movable in the vertical and horizontal directions and supports and permits the electric bending endoscope 11 to rotate in a direction around an axis.

The rotation in the direction around the axis of the electric bending endoscope 11 is performed in a rotation direction in which the electric bending endoscope 11 is rotated with a center of a virtual axis along an insertion direction of the insertion portion 13 of the electric bending endoscope 11. Specifically, in the present embodiment, the rotation direction of the electric bending endoscope 11 along the axis is a direction along the arrow R2 shown in FIG. 2.

For the purpose, the supporting portion 42 is configured of a bearing portion 42a (see FIG. 4) which is formed in a substantially annular shape, functions as first supporting means and a first supporting portion for rotatably supporting the bending drive unit 12 in the direction along the arrow R2 of FIG. 2, and is composed of a bearing member, a first arm portion 42b which functions as a first arm member for fixing the bearing portion 42a at a distal end, a ball joint 42c which is provided at a proximal end side of the first arm portion 42b and functions as second supporting means and a second supporting portion for supporting the first arm portion 42b rotatably in vertical and horizontal directions, a second arm portion 42d which fixes and supports the ball joint 42c at a distal end and functions as a second arm member, and a proximal end portion 42e to which a proximal end side of the second arm portion 42d is consecutively provided and provided in the vicinity of a distal end of the arm movable portion 43.

The bearing portion 42a is provided as the first supporting means and the first supporting portion which supports and permits the electric bending endoscope 11 to rotate in the direction around the axis.

On the bearing portion 42a, as shown in FIG. 4, an outer circumference of the bending drive unit 12 is provided in an engaged manner. At a distal end side of the bending drive unit 12, a retaining member 42aa is attached. Thus, the bearing portion 42a rotatably supports the bending drive unit 12.

Since the bending drive unit 12 and the insertion portion 13 can be detached, for example, after the electric bending endoscope 11 is used, while the heavy bending drive unit 12 is remained to the endoscope supporting device 40, only the insertion portion 13 can be detached and only the insertion portion 13 can be washed.

The electric bending endoscope 11 is used in a state that the bending drive unit 12 engages with the bearing portion 42a. During the usage, if the insertion portion 13 of the electric bending endoscope 11 is twisted or the like, the bending drive unit 12 which is consecutively provided with the insertion portion 13 freely and smoothly rotates in a same direction as the insertion portion 13 by the bearing portion 42a.

As described above, the second arm portion 42d is rotatable in the vertical and horizontal directions with respect to the arm movable portion 43 by the operation of the ball joint 42c which is provided at the proximal end portion. Accordingly, the electric bending endoscope 11 (the bending drive unit 12 of the electric bending endoscope 11) which is supported through the bearing portion 42a at the distal end of the supporting portion 42 can smoothly and freely move in either vertical or horizontal direction.

That is, the ball joint 42c is provided as the second supporting means and the second supporting portion for movably supporting the electric bending endoscope 11 in the vertical and horizontal directions.

Further, the ball joint 42c of the supporting portion 42, when the endoscope supporting device 40 is in the usage state, can support the first arum portion 42b to be rotatable in the vertical and horizontal directions with respect to the arm movable portion 43. This enables to ensure a degree of freedom of the movement of the electric bending endoscope 11 which is supported at the distal end side of the supporting portion 42.

On the other hand, when the endoscope supporting device 40 is in the usage standby state, the ball joint 42c of the supporting portion 42 works to regulate a free displacement of the supporting portion 42 (the first arm portion 42b). Accordingly, the movement of the electric bending endoscope 11 is regulated and the electric bending endoscope 11 is fixed and supported in a state in which the movement is regulated in the predetermined sate (the state of FIG. 3).

For the purpose, the ball joint 42c has a rotation regulation portion which functions as rotation regulation means for regulating the displacement. Configuration of the ball joint 42c and the rotation regulation portion which functions as the rotation regulation means will be described below.

As shown in FIGS. 5 to 7, a rotation regulation mechanism 41 which functions as the rotation regulation portion of the ball joint 42c includes a ball joint housing 41a which rotatably supports a proximal end side of the ball joint 42c, a rotation ring 41b which is integrally provided with the ball joint housing 41a with a screw or the like, a set collar 41c which rotatably and pivotally supports the rotation ring 41b and which is composed of an annular member, and the like.

As shown in FIG. 6, the ball joint housing 41a includes two substantially half-moon shaped members. The two members are integrally formed with screws 41ab. In substantially central portion of the ball joint housing 41a in which the two members are integrally formed, a space is formed such that the ball joint 42c can be rotatably engaged.

The ball joint housing 41a also includes a click mechanism 61 as shown in FIG. 6. The click mechanism 61 includes a click ball 61a, an urging member 61b which urges the click ball 61a, a pressure member 61c which supports the urging member 61b, and the like. The respective members (61a, 61b, 61c) are respectively disposed in a groove 61d which is formed from an outer circumference surface of the ball joint housing 41a toward a central axis.

At a predetermined corresponding portion on the outer circumference surface of the ball joint 42c, a click groove 42ca is formed. The click ball 61 of the click mechanism 61 can be detached with respect to the click groove 42ca of the ball joint 42c. Accordingly, when the click ball 61 engages with the click groove 42ca, the ball joint 42c cannot rotate with respect to the ball joint housing 41a. When the click ball is not engaged with the click groove 42ca, the ball joint 42c can rotate with respect to the ball joint housing 41a.

To the ball joint housing 41a, the rotation ring 41b is integrally provided by a screw 41aa. At a back side (arrow U side in FIG. 5) of the rotation ring 41b, at a substantially central portion of the rotation ring 41b, a cylinder-shaped protruding portion 41ba is provided. The convex portion 41ba rotatably fits into a hole which is formed at a substantially central portion of the set collar 41c which will be described below. The rotation ring 41b is pivotally supported with respect to the set collar 41c using a screw 41ca through a spacer 41cb with respect to the convex portion 41ba which fits into the substantially central portion.

A predetermined portion of an outer circumference surface side of the set collar 41c is fixed with respect to a vicinity of a distal end portion of the first arm portion 42d by a screw 42da. Thus, the ball joint housing 41a and the rotation ring 41b can rotate with respect to the set collar 41c which is fixed to the first arm portion 42d.

As shown in FIG. 7, in the set collar 41c, a part of the annular from the outer circumference surface to an inner circumference portion is formed to be divided. In the divided groove portion 41cc, a click ball position adjustment handle 41d is provided. The click ball position adjustment handle 41d is a screw-shaped member extending from one side of the divided groove portion 41ca through the divided groove portion 41ca to the other side. Fastening the click ball position adjustment handle 41d narrows the gap of the divided groove 41ca to enable the set collar 41c to fasten the convex portion 41ba of the rotation ring 41b. Accordingly, when the click ball position adjustment handle 41d is loosened, the ball joint housing 41a and the rotation ring 41b can rotate with respect to the set collar 41c. On the other hand, when the click ball position adjustment handle 41d is fastened, the ball joint housing 41a and the rotation ring 41b are fixed and supported with respect to the collar 41c. Thus, the portion of the click mechanism 61 of the ball joint housing 41a can be set and disposed at any position.

The arm movable portion 43 and the slide guide 44 are provided as second moving means and a second movement member which can move the electric bending endoscope 11 which is supported by the supporting portion 42 with respect to the floor in the horizontal direction.

The arm movable portion 43 is provided such that the arm movable portion 43 can smoothly slide with respect to the slide guide 44 in a direction along the arrow X of FIG. 2. In such a case, the slide guide 44 functions to guide the arm movable portion 43 to move in a predetermined direction (arrow X direction).

The slide guide 44 is consecutively provided with the arm fixing member 45 through the hinge 46. The hinge 46 supports the slide guide 44 such that the slide guide 44 can rotate in a direction along the arrow W of FIG. 3 within a predetermined range with respect to the arm fixing member 45. That is, the hinge 46 is provided as first moving means and a first movement member which can move up and down the electric bending endoscope 11 which is supported at the distal end side of the arm portion 40a in a vertical direction with respect to the floor.

Now, an attachment portion of the hinge 46 is described in detail with reference to FIGS. 8 and 9.

The hinge 46 includes one arm portion 46a which is fixed at one end portion of a proximal end side of the slide guide 44, the other arm portion 46b which is fixed at one end portion of an arm fixing member 45, and a joint portion 46c which rotatably and consecutively provides the one arm portion 46a and the other arm portion 46b with each other.

Further, the joint portion 46c of the hinge 46 includes, although not shown in the drawings, a damper mechanism or the like which prevents the second moving means (second moving member) which has the arm movable portion 43 and the slide guide 44 from rapidly rotating in the direction along the arrow W of FIG. 3.

At one side surface of the joint portion 46c, a hinge angle adjustment mechanism 57 is provided. The hinge angle adjustment mechanism 57 enables the arm movable portion 43 and the slide guide 44 to maintain predetermined angles.

The hinge angle adjustment mechanism 57 includes a click board 57a, a click ball 57b, and a leaf spring 57c.

On the click board 57a, a click ball housing hole 57d for housing the click ball 57b is formed. In the click ball housing hole 57d, the click ball 57b is housed. On the click board 57b, the leaf spring 57c which functions as a plate-shaped urging member is mounted by a screw or the like to cover an opening of an outer surface side of the click ball housing hole 57d. In the state, when the click ball 57b is housed in the click ball housing hole 57d, the click ball 57b is disposed such that the click ball 57b slightly protrudes from the other opening of the click ball housing hole 57d toward the one side surface of the joint portion 46c.

The click board 57a is fixed on a side surface of one end portion of a proximal end of the slide guide 44 by a screw 44a, for example. Then, one surface of the click board 57a is disposed to come in contact with the one end of the joint portion 46c of the hinge 46. Thus, when the slide guide 44 rotates in the direction along the arrow W shown in FIG. 3 or FIG. 8 by the operation of the hinge 46, in conjunction with the rotation, the click board 57a also rotates in the same direction, and the click board 57a slides with respect to the one side surface of the joint portion 46c.

As described above, when the click board 57a is attached on the slide guide 44, the other opening of the click ball housing hole 57d is covered by the one side surface of the joint portion 46c of the hinge 46.

That is, the click ball 57b is disposed in the click ball housing hole 57 and in the state that the click ball 57b is tightly held in the space between the leaf spring 57c and the one side surface of the joint portion 46c. Then, the protruding portion of the click ball 57b is pressed by the one side surface of the joint portion 46c. The pressure 57c works as a force to press the leaf spring 57c through the click ball 57b. Thus, the urging force of the leaf spring 57c works as a repulsive force for urging the click ball 57b to the side of the one side surface of the joint portion 46c.

On the other hand, on the one side surface of the joint portion 46c, that is, on the surface where the click board 57a comes in contact with, a plurality of crick grooves 64d in which the protruding portion of the click ball 57b which moves in conjunction with the movement of the click board 57a engages with are formed. That is, in each click groove 46d, the click ball 57b which moves along the one side surface of the joint portion 46c together with the click board 57a in response to the rotation operation of the slide guide 44 can engage in each case. The click groves 46d are provided in a circumferential shape at positions along a rotation path of the click ball 57b.

In the present embodiment, the click grooves 46d are formed at two positions, that is, the position corresponding to the usage state and the position corresponding to the usage standby state. However, it is not limited to the above, but, in addition to the above, the click groove 46d may be formed, for example, at a predetermined position between the position corresponding to the usage state and the position corresponding to the usage standby state. Thus, the arm movable portion 43 and the slide guide 44 can be held midway between the usage state and the usage standby state, that is, the arm movable portion 43 and the slide guide 44 can be held in an inclined state, and then, the endoscope can be used in the state.

In the state that the click ball 57b engages with the click groove 46d, an angle of the hinge 46 is fixed. Thus, the arm movable portion 43 and the slide guide 44 are positioned and fixed at predetermined positions respectively, and the positions are maintained.

On the other hand, in the state, if an external force exceeding a predetermined amount is applied to the arm movable portion 43 and the slide guide 44, the click ball 57b is detached from the click groove 46d. Then, for example, the hinge 46 (the arm movable portion 43 and the slide guide 44) freely rotates until the click ball 57b engages with a neighbor click groove 46d.

At the same time, when the second state (state shown in FIG. 3; usage state) that the arm movable portion 43 and the slide guide 44 stand substantially perpendicularly to the floor is changed (release an attracting state of the first magnet 47 and the second magnet 48 which will be described below) to the first state (state shown in FIG. 2; usage state) by rotating the arm movable portion 43 and the slide guide 44 in the direction along the arrow W of FIG. 3, the arm movable portion 43 and the slide guide 44 can rotate in the same direction. Then, the hinge angle adjustment mechanism 57 provided in the vicinity of the hinge 46 also works to prevent the arm movable portion 43 and the slide guide 44 from rapidly rotating in a predetermined direction (W direction of FIG. 8).

FIGS. 8 and 9 illustrate states of the hinge 46 and the hinge angle adjustment mechanism 57 when the arm movable portion 43 and the slide guide 44 are in the usage standby state (state shown in FIG. 3).

Returning to FIGS. 2 and 3, the first magnet 47 of the side of the arm fixing member 45 and the second magnet 48 of the side of the arm movable portion 43 are disposed such that when the endoscope supporting device 40 is in the state shown in FIG. 3, that is, when the electric bending endoscope 11 is in the usage standby state, the first magnet 47 and the second magnet 48 attract each other. As shown in FIG. 3, when the first magnet 47 and the second magnet 48 attract each other, the arm fixing member 45 and the arm movable portion 43 are disposed in a substantially linear state and stand perpendicularly to the floor.

At the same time, the constant force spring 49 is provided consecutively between the arm movable portion 43 and the fourth magnet 51 when the arm portion 40a is in the state (usage standby state) shown in FIG. 3 to prevent the arm portion 40a from rotating with respect to the supporting portion 40b.

For the purpose, as described above, the proximal end side of the constant force spring 49 is fixed on the one surface of the proximal end side of the arm movable portion 43. Further, at a distal end of the constant force spring 49, the third magnet 50 is provided. When the arm portion 40a is in the state (usage standby state) shown in FIG. 3, the third magnet 50 attracts the fourth magnet 51.

The supporting portion 40b in the endoscope supporting device 40 includes a leg portion 53 which has a caster 52, a first support rod 54 which is perpendicularly supported by the leg portion 53, the second support rod 55 provided extensively with respect to the first support rod 54, a fixing handle 56 which fixes the second support rod 55 with respect to the first support rod 54, and the like.

Accordingly, when the endoscope supporting device 40 is in the usage standby state, the height adjustment is performed such that the second support rod 55 is extended or contracted with respect to the first support rod 54, and then, the second support rod 55 is fixed with respect to the first support rod 54 by the fixing handle 56 at any position. Thus, when the endoscope supporting device 40 is in the usage standby state, the positional adjustment in the height direction of the supporting portion 42 can be performed. Accordingly, it is possible to arbitrarily set the vicinity of the distal end portion of the insertion portion 13 of the electric bending endoscope 11 which is held by the supporting portion 42 not to come in contact with the floor.

The electric bending endoscope 11 which is supported by the arm portion 40a is, when the endoscope supporting device 40 is in the usage standby state as shown in FIG. 3, fixed in a state that the arm portion 40a supports the electric bending endoscope 11. Then, the position of the supporting portion 42 which supports the bending drive unit 12 of the electric bending endoscope 11 is fixed by the fixing handle 56 at any position by extending or contracting the second support rod 55 with respect to the first support rod 54 as described above. Thus, the distal end portion of the insertion portion 13 of the electric bending endoscope 11 is set to a position not come in contact with the floor.

On the other hand, when the endoscope supporting device 40 is in the usage state shown in FIG. 2, the electric bending endoscope 11 supported by the arm portion 40a can move in the vertical and horizontal directions by the arm portion 40a. At the same time, the endoscope supporting device 40 can move on the floor by the caster 52.

An operation of thus configured electric bending endoscope device 1 according to the present embodiment will be described below.

In order to displace the endoscope supporting device 40 from the usage standby state (FIG. 3) to the usage state (FIG. 2), the arm movable portion 43 and the slide guide 44 are rotated in the direction of the arrow W1 of FIG. 3 by one operation.

In such a case, first, a user rotates the arm movable portion 43 and the slide guide 44 in the direction of the arrow W1 of FIG. 3. Then, the attracted state of the first magnet 47 and the second magnet 48 is released. At the same time, the attracted state of the third magnet 50 and the fourth magnet 51 is released. Further, at the same time, the engaged state of the hinge 46 by the hinge angle adjustment mechanism 57 is also released. Then, the damper mechanism of the hinge 46 prevents the arm movable portion 43 and the slide guide 44 from rapidly rotating in the direction of the W. In the usage state of FIG. 2, the hinge angle adjustment mechanism 57 of the hinge 46 is positioned at a corresponding position and an engaged state is ensured. Thus, the arm movable portion 43 can move in the direction along the slide guide 44.

In the state, to the bending drive unit 12 which is supported by the supporting portion 42, a force due to the weight of the bending drive unit 12 is applied in a direction to rotate the first arm portion 42b. Thus, the click mechanism 61 by the rotation regulation mechanism 41 of the ball joint 42c of the supporting portion 42 is released. Then, the ball joint 42c can freely rotate.

The user may apply some amount of force to the bending drive unit 12 in a direction for rotating the first arm portion 42b.

As described above, the electric bending endoscope 11 can move in the direction of the arrow X of FIG. 2 while being rotatably and pivotally supported in the direction of the arrow R2 of FIG. 2, and the arm portion 40a can rotate in the direction of the arrow R1 of FIG. 2. Accordingly, the electric bending endoscope 11 also ensures the state rotatable in the similar direction.

On the other hand, in order to displace the endoscope supporting device 40 from the usage state (FIG. 2) to the usage standby state (FIG. 3), the arm movable portion 43 and the slide guide 44 are rotated in the direction of the arrow W2 of FIG. 3 by one operation.

In such a case, first, the user rotates the arm movable portion 43 and the slide guide 44 from the state of FIG. 2 to the direction of the arrow W2 of FIG. 3. When the arm movable portion 43 and the slide guide 44 are in a substantially linear state as shown in FIG. 3, and stand perpendicularly to the floor, to the bending drive unit 12 which is supported by the supporting portion 42, a force due to the weight of the bending drive unit 12 is applied in a direction to rotate the first arm portion 42b. Thus, the click mechanism 61 by the rotation regulation mechanism 41 of the ball joint 42c of the supporting portion 42 is in an engaged state. Then, the ball joint 42c is in a rotation regulation state.

Then, the first magnet 47 and the second magnet 48 enter in an attracted state. At the same time, the third magnet 50 and the fourth magnet 51 also enter in the attracted state. Further, at the same time, the hinge adjustment mechanism 57 of the hinge 46 ensures an engaged state at a corresponding position. Thus, the arm movable portion 43 and the slide guide 44 are substantially in parallel with the support rods (54, 55) of the supporting portion 40b, and the movement and the rotation are regulated. Then, the state enters in a usage standby state that the bending drive unit 12 is fixed and supported while the distal end portion of the insertion portion 13 of the electric bending endoscope 11 does not come in contact with the floor.

As described above, according to the present embodiment, the endoscope supporting device 40 can switch between the two modes, that is, the usage state shown in FIG. 2 that while the bending drive unit 12 of the electric bending endoscope 11 is supported, an observation or a treatment of the inside of a body cavity of a subject is performed using the electric bending endoscope 11, and the usage standby state shown in FIG. 3 that while the bending drive unit 12 of the electric bending endoscope 11 is supported and the distal end portion of the insertion portion 13 does not come in contact with the floor, the movement of the electric bending endoscope 11 is regulated to stand by. In such a case, the switching of the two modes of the usage state and the usage standby state can be very readily and surely realized by the one operation that the arm movable portion 43 and the slide guide 44 which constitute a part of the arm portion 40a are rotated in the predetermined direction (the direction of the arrow W of FIG. 3).

In the above-described embodiment, the endoscope supporting device 40 is independently provided. However, it is not limited to the above, but, for example, the support rod portions (lower support rod portions, caster, or the like) of the endoscope supporting device 40 may be omitted, and the proximal end portion of the movable arm may be fixed to a part of the cart 20. The cart 20 in the above-described embodiment can move on the floor with the caster. Accordingly, such a configuration may include a similar function to the above-described endoscope supporting device 40.

As described above, according to the present invention, while the electric bending endoscope is always supported, the electric bending unit and the insertion portion can be attached or detached. After an inspection, only the insertion portion may be detached and washed. Accordingly, the operation of attaching or detaching the electric bending unit to/from the supporting device may be omitted. Further, the operation of attaching a universal code along the arm or detaching the universal code may be omitted. Accordingly, the efficiency in the operations to be performed before and after the inspection can be improved and the labor or burdens can be reduced. Further, a same supporting device adapted to the inspection use can also be used for storage, the efficiency in the storage space can be improved.

This application claims priority from Japanese Patent Application No. 2005-071713 filed on Mar. 14, 2005, the disclosed contents of which are incorporated herein by reference in descriptions of the present invention, claims, and drawings.

The invention claimed is:

1. An electric bending endoscope device comprising:
   an endoscope having an observation function and a treatment function of the inside of a body cavity;
   an endoscope supporting device having a first moving member capable of moving the endoscope up and down in a direction perpendicular to a floor, a second moving member capable of moving the endoscope in a horizontal direction with respect to the floor, a first supporting portion for permitting the endoscope to rotate around an axis and supporting the endoscope, and second supporting portion for supporting the endoscope movably in vertical and horizontal directions;

an arm fixing member which is rotatably provided with respect to a supporting portion and connected with the second moving member through the first moving member;

a first magnet which is fixed on one surface of the arm fixing member;

a second magnet which is fixed on a proximal end surface of the second moving member;

a thin-plate shaped constant force spring whose one end is fixed on one surface of the proximal end side of the second moving member;

a third magnet which is provided at a distal end side of the constant force spring; and a fourth magnet which is fixed on the supporting portion, wherein when the endoscope supporting device is in the usage standby state, the third magnet attracts the fourth magnet which is to be attracted by the third magnet to fix the second moving member and the second supporting portion, and the state is maintained.

2. An electric bending endoscope device comprising:

an endoscope having an observation function and a treatment function of the inside of a body cavity;

an endoscope supporting device having a first moving member capable of moving the endoscope up and down in a direction perpendicular to a floor, a second moving member capable of moving the endoscope in a horizontal direction with respect to the floor, a first supporting portion for permitting the endoscope to rotate around an axis and supporting the endoscope, and second supporting portion for supporting the endoscope movably in vertical and horizontal directions;

an elongated insertion portion to be inserted into the body cavity;

a bending drive unit, supported by the endoscope supporting device, the bending drive unit being detachably and consecutively provided at a proximal end side of the insertion portion and includes an electric bending drive member in the bending drive unit;

an operation portion which is provided separately from the bending drive unit and electrically connected with the bending drive unit;

an arm fixing member which is rotatably provided with respect to a supporting portion and connected with the second moving member through the first moving member;

a first magnet which is fixed on one surface of the arm fixing member;

a second magnet which is fixed on a proximal end surface of the second moving member;

a thin-plate shaped constant force spring whose one end is fixed on one surface of the proximal end side of the second moving member;

a third magnet which is provided at a distal end side of the constant force spring; and a fourth magnet which is fixed on the supporting portion, wherein when the endoscope supporting device is in the usage standby state, the third magnet attracts the fourth magnet which is to be attracted by the third magnet to fix the second moving member and the second supporting portion, and the state is maintained.

* * * * *